US008888971B1

(12) United States Patent
Radomyshelsky et al.

(10) Patent No.: US 8,888,971 B1
(45) Date of Patent: Nov. 18, 2014

(54) DYNAMIC PRECIOUS METAL ASSAY DEVICE

(71) Applicants: Leonid Radomyshelsky, San Diego, CA (US); Boris Loginov, San Diego, CA (US)

(72) Inventors: Leonid Radomyshelsky, San Diego, CA (US); Boris Loginov, San Diego, CA (US)

( * ) Notice: Subject to any disclaimer, the term of this patent is extended or adjusted under 35 U.S.C. 154(b) by 94 days.

(21) Appl. No.: 14/144,039

(22) Filed: Dec. 30, 2013

(51) Int. Cl.
*G01N 27/28* (2006.01)
*G01N 27/26* (2006.01)

(52) U.S. Cl.
CPC ..................................... *G01N 27/26* (2013.01)
USPC ......... 204/400; 205/790; 422/82.02; 324/693

(58) Field of Classification Search
USPC .................. 204/400, 416–419; 205/790, 795; 422/82.02, 408, 430; 401/198, 203, 401/204, 205, 206; 436/80; 324/446, 450, 324/437, 691, 693, 696, 724
See application file for complete search history.

(56) References Cited

U.S. PATENT DOCUMENTS

| 4,799,999 | A | 1/1989 | Medvinsky et al. |
| 5,128,016 | A | 7/1992 | Moment et al. |
| 5,218,303 | A | 6/1993 | Medvinsky |
| 6,051,126 | A | 4/2000 | Fegan, Jr. |
| 6,766,817 | B2 | 7/2004 | da Silva |
| 2008/0078677 | A1* | 4/2008 | Chua et al. ................. 204/406 |
| 2013/0220807 | A1 | 8/2013 | Radomyshelsky et al. |

* cited by examiner

*Primary Examiner* — Luan Van
*Assistant Examiner* — Gurpreet Kaur
(74) *Attorney, Agent, or Firm* — Selwyn S Berg

(57) ABSTRACT

A synergistic improvement of a precious metal assaying device with its associated electronic decoding algorithms further employing a precise feed of an electrolyte from a disposable flexing cartridge and through porous media for conveying electrolyte to create a reproducible electrochemical contact by a wetting action between a reference electrode in the assaying device and an external specimen under test where the electrolyte is passed through a novel slit diaphragm permitting efflux of electrolyte and reflux of unused electrolyte that results in a self-cleaning flush of the assaying device. The synergistic slit diaphragm permits the flow of electrolyte from the flexing cartridge in response to the positive pressure and the cleansing return of unused electrolyte on negative pressure of the cartridge, thereby solving a contamination problem which was a major shortcoming in such assaying devices.

3 Claims, 2 Drawing Sheets

The Pencil Assembly
and External Electronics Box

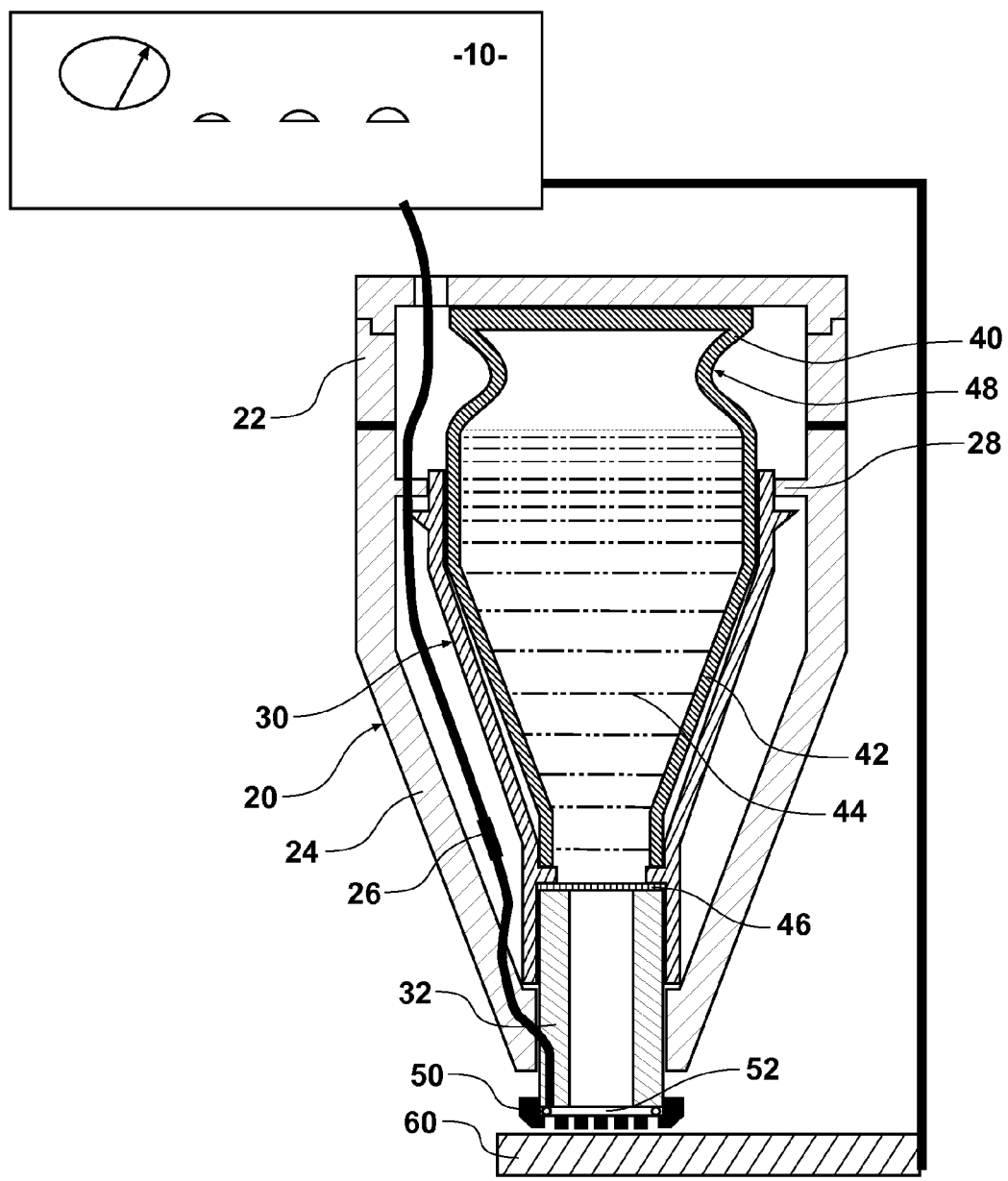
Figure 1 - The Pencil Assembly and External Electronics Box

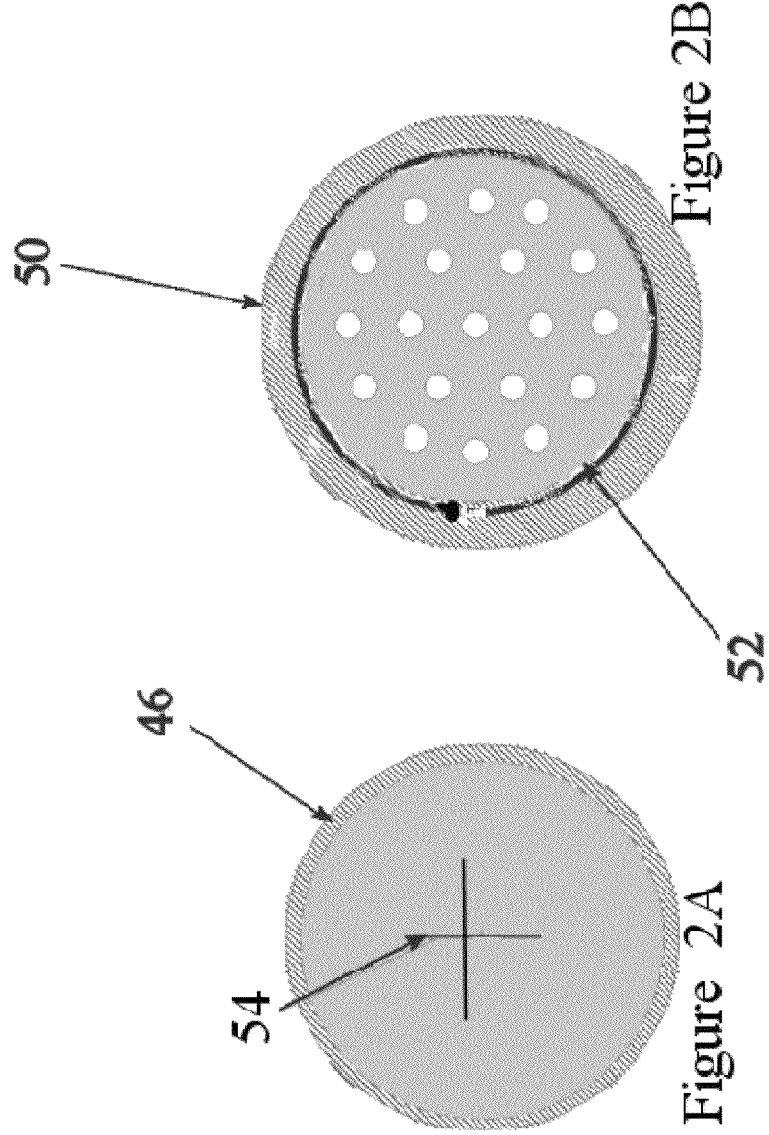
FIGURES 2A POROUS CAP ASSEMBLY 50 AND 2B THE SLIT DIAPHAM 46
Figures 2A Porous Cap Assembly 50 and 2B the Slit Diaphragm 46 illustrating a plan views of the Porous Cap Assembly 50 and the cross cut Slit Diaphragm 46

DYNAMIC PRECIOUS METAL ASSAY DEVICE

REFERENCES CITED

U.S. Patent Documents

U.S. Pat. No. 4,799,999 January 1989: DYNAMIC PRECIOUS METAL ASSAY METHOD
U.S. Pat. No. 5,218,303 January 1993: BROAD SPAN DYNAMIC PRECIOUS METAL ASSAY METHOD BY DRIVING ELECTRICAL PULSES THOUGHT AN ELECTROLYTE WET JUNCTION.
U.S. Pat. No. 6,051,126 April 2000: METHOD FOR ANALYZING PRECIOUS METALS
U.S. Pat. No. 5,128,016 July 1992: PRECIOUS METAL ANALYZER APPARATUS
U.S. Pat. No. 6,766,817 June 2004: FLUID CONDUCTION UTILIZING A REVERSIBLE UNSATURATED SIPHON WITH TUBARC POROSITY ACTION

OTHER PUBLICATIONS

Book

Dynamics Of Fluids In Porous Media By Jacob Bear, ©1972 Published by Dover 1988, ISBN 0-486-65675-6. Maria Claudia Ferreira Drumond de Sousa at MIT academically studied the inherent features of the slit diaphragm based on physics.

REFERENCE ARTICLES ON INTERNET

"ScrapGoldGuru.com, How to Make Money with Scrap Gold" http://www.scrapgoldguru.com/electronic-gold-tester-review.
"Gold Testing Guide-electronic gold testers 101" by Igem: "Electronic Gold Tester Review" http://reviews.ebay.com/Gold-Testing-Guide-electronic-gold-testers-101?ugid=10000000004085705

PUBLISHED APPLICATION

US-2013-0220807-A1 of Aug. 29, 2013. DYNAMIC PRECIOUS MEAL ASSAY DEVICE

BACKGROUND

The company, Tri-electronics Incorporated pioneered the now popular electronic gold testers used throughout the world. The Company held the basic parent patent, DYNAMIC PRECIOUS METAL ASSAY METHOD, U.S. Pat. No. 4,799,999 of Jan. 24, 1989 which was a novel method which utilized the complex chemistry of time dependant electrochemistry to determine the gold content of an alloy specimen sample in units of karats. The ongoing research, guided by worldwide customer feedback has resulted in the decision to go to insertable disposable cartridges as a unique approach to improve the basic patent, U.S. Pat. No. 4,799,999. Their newest cartridge style electronic gold tester is the subject of Published Application US-2013-0220807-A1 of Aug. 29, 2013; DYNAMIC PRECIOUS METAL ASSAY DEVICE An excellent review of current electronic gold testers has been videotaped as a youtube™ internet presentation Gold Testers Review—Find the best gold tester for you by igemcorp Dec. 5, 2012 http://www.youtube.com/watch?v=1kd0xIdwg3U and clearly designates Tri-electronics products as the best professional gold tester on the market that uniquely uses disposable cartridge inserts of environmentally and personal safe reagents. Published Application US-2013-0220807-A1 of Aug. 29, 2013; DYNAMIC PRECIOUS MEAL ASSAY DEVICE, incorporated by reference, details the objectives of the Company R&D program of improvement of product and states these research objectives as being—

A precision and controlled feed of the electrolyte solution was needed to avoid costly waste and staining. This is now accomplished by two systems:
a) a threaded shaft which drives a piston in a cartridge;
b) an accordion springing cartridge that is pinched; where either cartridge is engaged by a rotating screw on the closure cap. The screw pitch of is designed to meter out the exact amount of electrolyte to the galvanic cell.

The electrolyte is contained in a sealed disposable cartridge, so no electrolyte is ever handled in bulk. This avoids contamination and costly spills of a toxic material as well as waste disposal control.

The body of the gold tester is a rugged casing which holds the disposable cartridge in a locked position and also has a removable porous cap tip. The casing encloses a wire feed channel for the reference electrode wire that goes to the tip where the reference electrode wire is circumferentially wrapped into the reference electrode in the removable porous cap which comprises the galvanic cell.

A removable porous cap is attached to the bottom of the casing. This porous cap is capable of holding electrolyte by surface tension and capillary action in and on its porous surface. The perforated mesh or pattern on the bottom of the cap is to be positioned against the test specimen. This system assures uniformity of specimen contact of a repeatable wetted contact with the specimen electrode as well as tight control of the geometry of the galvanic cell.

The insertable accordion springing cartridge that was being laboratory tested was collapsed by a screw driven piston was further developed for various reasons and experienced major changes that constitutes new matter in the within application. The overall design of this novel improvement to meet the above objectives is so comprehensive as to require a new application as an improvement on the parent U.S. Pat. No. 4,799,999 of Jan. 24, 1989. The modification of the electronic pencil system now uses a resilient casing closure top which limits the stroke of the inserted pipette cartridge thereby insuring an accurate expulsion of electrolyte through a slit diaphragm at the bottom of the cartridge. The spring-like restoring action of the cartridge and top permits volumetric replacement of expelled electrolyte and also assures any extraneous electrolyte clinging to the effluent exit is reduxed into the cartridge which contributes to a self-cleaning action as well as conservation of the electrolyte. Moreover, the resilient casing top closure cap is easily removed making the insertable cartridge much more accessible for replacement. The new pencil is also much easier to manufacture making the product more competitive with the lower quality electronic gold testers on the market, but still holding to the high quality and dependability that Tri-electronics Corp has earned.

BRIEF SUMMARY OF THE INVENTION

The objective of the within preferred device embodiment for the methodology of the parent U.S. Pat. No. 4,799,999 takes into account minimizing the cost of manufacturing the device as well as increasing the accuracy and alloy sensitivity.

The interpolating algorithm to determine the karat assay should also be kept as simple and direct as possible. The objective achieved in the within specification is a dependable device for accurately professionally assaying gold samples that range to over 20 karat The final prototypes are shown in the drawings and further described in this following specification.

Tri-Electronics engaged in a R&D program after the granting of the method parent patent DYNAMIC PRECIOUS METAL ASSAY METHOD, U.S. Pat. No. 4,799,999 of Jan. 24, 1989. The company examined the competitive products on the market and also had feedback from its customers. Based on all the information as well as the experimental program, it was realized that the corrosive electrolyte inevitably caused accelerated decay of any permeable wicking material intended to transport the electrolyte to the tip. In addition, the placement of the active part of the reference electrode at a relatively large distance from the test specimen electrode resulted in a polarization of the reference electrode as well as ionic depletion of the residual electrolyte between the reference electrode and the specimen sample electrode and within any permeable wick media. The uncertain geometry of the galvanic cell surface wetting of the specimen does invalidate the algorithm of the electronic readout resulting in inaccurate readings. A further problem was the potential contamination of the electrolytic substance in a bulk container. The electrolyte dispensing system on the existing gold testing devices was also a bit sloppy and not well controlled, resulting in costly waste of the electrolyte. Often, this sloppiness resulted in a varying pattern of contact with the specimen sample and staining of a valuable piece of jewelry. Cleaning of the marketed gold testers was also difficult and really a factory maintenance operation. A more critical problem was that the accuracy of the instruments was poor at high gold karat values, which is the assay range is of greatest interest for professional users. Extensive experimentation clearly indicated that the sensitivity of the metric increased as the dimensions of the galvanic cell became smaller. This necessitated a program of testing various electrode geometries so as to assure close tolerances and repeatability of each test procedure. The herein proposed improvement device embodiment on the method of the parent U.S. Pat. No. 4,799,999 is the end result of this extended R&D program and speaks to the current optimization of the marketable product.

The first phase of the R&D program resulted in the realization of the use of porosity phenomena in preference to wicking in a permeable material. Important characteristics of wicking have been academically discussed in such Reference materials as U.S. Pat. No. 6,766,817. The realization of the distinction between porosity and wicking and the adoption of porosity in preference to the classic use of wicking in this device resulted in the construction of a miniaturized electrolytic cell of highly controlled geometry in respect to a reference electrode in said miniaturized electrolytic cell and the tested specimen of gold. The tight geometry assures accurate high value karat analysis and reproducibility of results.

The utilization of a miniature galvanic cell results from the novel porous effluent cap affixed to the bottom of the sensing pencil. The technical subject of porosity is well covered in the seminal engineering text of *Dynamics Of Fluids In Porous Media* by Jacob Bear, ©1972 Published by Dover 1988, ISBN 0-486-65675-6. The importance of porosity is that a porous material holds liquids and is technically distinguishable from a permeable material which transports liquids. Porosity is a characteristic feature of sponges, chamois and blotters; permeability is a characteristic of felt, cotton and other fiber materials intended as wicks. Because of the physics of capillary action and surface tension it is very difficult to wash clean a permeable material and much easier to flush a porous material. In the within embodiment, the feature of flushing the used electrolyte is critical in maintaining the accuracy of this precious metal tester. The flushing is a consequence of the redux of the electrolyte back into the cartridge. Hence, the importance of porosity for holding a repeatable small quantity of electrolyte for a wetting contact with the external test specimen. The ability to easily replace the porous cap is also critical. Though porous media is generally available, it is best to manufacture a porous cap by a precision pattern of perforations in a material known to be inert to the electrolyte. Moreover, the corrosive action of the electrolyte did result in the contamination and destruction of all the usual permeable wicks and often requiring factory replacement. This serious problem is alleviated by the elimination of wicking material.

The novelty of the within improvement results from the serendipitous discovery of a slit diaphragm. The initial concept of a syringe insertable container from which the contained electrolyte is expelled by a precision screw drive had problems of leakage from the insertable cartridge exit hole. The initial work was essentially based upon the concept of the dropper bottle which retains liquids as a consequence of surface tension and air pressure. Such dropper bottles expel their liquid contents on being squeezed. However, the use of dropper bottles of electrolyte for electronic gold testers has been shown to be sloppy, wasteful and potentially hazardous. It was noted that an insertable cartridge dropper bottle architecture wept/leaked electrolyte from the tip when not in use.

The solution to this problem required a valve on the effluent exit of the insertable cartridge dropper bottle. Trial and error finally resulted in what is called a slit diaphragm and has been the objective of much research. The unique characteristics of the slit diaphragm was discovered in the physiology of the kidneys and remained a subject of biological interest until Maria Claudia Ferreira Drumond de Sousa at MIT academically studied the inherent features of the slit diaphragm based on physics. The important feature of the slit diaphragm is that it is a full closure flapping valve that responds to pressure and expels individual droplets of uniform size to each quantum of pressure. The amount of liquid expelled from the container depends on the elastic characteristics of the diaphragm material, the length of the slit and the amount of pressure caused by the squeezing of the insertable cartridge container. This serendipitous discovery in combination with the uniquely developed miniature galvanic cell discussed in the Published Application US-2013-0220807-A1 of Aug. 29, 2013 of this inventor gives the synergistic result of having a completely sealed insertable cartridge container that delivers an accurate amount of electrolyte into the said miniaturized galvanic cell for wetting a well defined geometry of a test specimen to determine its gold content. In addition, said slit diaphragm is inherently a two way valve and reopens on negative pressure to redux any excess electrolyte in the feed channel between the exit of the insertable cartridge dropper bottle and in the miniaturized galvanic cell, resulting in a self cleaning action following every test as well as conservation of electrolyte. Such self cleaning of the pencil and the specimen is very important in maintaining dependable readings of gold karats.

The complete system comprises
  A pencil assembly of a rugged casing with removable resilient cap and an interior chamber as a guide for an Insertable cartridge of electrolyte. The casing holds this insertable flexible disposable cartridge. The pencil also has a removable porous cap tip on the effluent side. The casing encloses a wire feed channel to the reference electrode wire which is in the tip. This reference electrode wire of platinum is circumferentially wrapped into the removable porous cap which comprises the galvanic cell.

External to the precious metal device sensor pencil assembly is the electronics program box which contains programmed circuitry to initiate electric pulses which are fed to the reference electrode wire and test specimen sample. There are three programs:
a) the charging program is to activate the galvanic cell;
b) the readout program to analyze the decay profile of the galvanic cell and annunciate its analysis in terms of karat content of the test specimen;
c) the depolarizing program of a reversed voltage pulse (in respect to charging program) to remove any residual electrolytic or reference electrode contamination that may occur in the galvanic cell.

The miniature galvanic cell structure is created within the attached porous cap when the test specimen is placed in contact with the bottom of the perforated mesh of the cap and there is electrolyte filling the cap and saturating the porous perforated mesh so as to also contact and wet the test specimen in a well defined geometry. The active galvanic cell is formed by the charging cycle from the electronics program box and that cell is between the ring of reference electrode wire and the test specimen sample. The karat is heuristically determined from the discharge electric voltage profile by an analytic program in the electronic program box.

Each test operation has been shown to be identical within the error guarantee of the device as a consequence of the reproducibility of each contact geometry that requires a highly controlled deposit of electrolyte and the stability of the chemical characteristics of the materials involved. The controlled amount of electrolyte deposited within the well defined wetted area is assured by this slit diaphragm and conservation of the materials is assured by the self cleaning action resulting from the two way action of said slit diaphragm. This new improved pencil device results from the novel synergy of the combination of a porous miniature galvanic cell, an insertable disposable cartridge flexible electrolytic container in a rugged casing with removable cap. In addition, the novel pencil has fewer parts making it easier to produce and hence less costly. It remains a tool intended for the professional market and has been shown to be the most accurate electronic gold tester in that market.

BRIEF DESCRIPTION OF THE DRAWINGS

FIG. 1, The Sensor Pencil Assembly and External Electronics Box is a central vertical cross sectioned view of the precious metal assay sensor pencil showing the details of the components of sensor pencil with its Top Cap 22, Casing 24, Disposable Cartridge Assembly 40, Porous Cap Assembly 50 cap, and external Electronics Program Box 10 with some ubiquitous Test Specimen Electrode 60 attached.

FIG. 2a Porous Cap Assembly 50 and 2b The Slit Diaphragm 46 show horizontal internal views. FIG. 2a shows the Porous Cap Assembly 50 which attaches to the bottom of the Casing 24 and encloses the Reference Electrode 52 of the galvanic cell FIG. 2b shows the The Slit Diaphragm 46 of a simple slit cross cut into the diaphragm which is located between the Insertable Disposable Cartridge Assembly 40 and the Electrolyte Feed Tube 32, shown in FIG. 1.

DETAILED DESCRIPTION AND MODE OF OPERATION

FIG. 1: The Sensor Pencil Assembly and External Electronics Box

The assembled DYNAMIC PRECIOUS METAL ASSAY DEVICE is depicted in FIG. 1. The major components are the Electronics Program Box 10, the Sensor Pencil Assembly 20 and the Porous Cap Assembly 50. Electronics Program Box, 10 contains the programs which comprise the algorithms for
a) charging the galvanic cell;
b) analyzing the voltage decay profile of the galvanic cell for annunciating its analysis in terms of karat content of the test specimen;
c) depolarizing the galvanic cell by generating a reversed voltage pulse thereby removing any reference electrode contamination.

The Sensor Pencil Assembly 20 comprises the elements of the Top Cap 22, a Casing 24, Casing Wire 26, Retaining Ribs 28, Cartridge Guide 30, and Electrolyte Feed Tube 32.

Into this is inserted the Insertable Disposable Cartridge Assembly 40 containing the Electrolyte 42. The Insertable Disposable Cartridge Assembly 40 has a Flexing Means which is best practiced herein as an Accordion Fold 48 near its top, and at the bottom is terminated with the Slit Diaphragm 46 that gives it the ability to reflux Electrolyte 44 distal to this Insertable Disposable Cartridge Assembly 40 so as to flush the lower section of the Sensor Pencil Assembly 20 and Porous Cap Assembly 50.

On the bottom of this Sensor Pencil Assembly 20 is the Porous Cap Assembly 50 which holds the circumferential platinum Reference Electrode 52 as shown in FIG. 2 in plan detail and discussed below.

The Test Specimen 60 can be any gold metal alloy item which the user needs to assay.

From this FIG. 1 DYNAMIC PRECIOUS METAL ASSAY DEVICE, the operation of the system is obvious. The Electronics Program Box 10 is not new and has been well covered in prior patents. It is further noted that the components of this novel system has been considerably reduced from those of all dependable gold testing and the components are more easily field or user replaceable as well as more economically produced.

The Test Specimen 60 should be cleaned of all its used deposits to expose a section of alloy and the bottom of the DYNAMIC PRECIOUS METAL ASSAY DEVICE, the Porous Cap Assembly 50, is pressed against the cleaned Test Specimen 60 and the center of the Top Cap 22 is depressed which causes the top of the Insertable Disposable Cartridge Assembly 40 to likewise collapse and expel an appropriate amount of Electrolyte 42 wetting the Test Specimen 60. An appropriate button is pushed on the Electronics Program Box 10 and a polarizing charge is transmitted through the Casing Wire 20 to the Reference Electrode 52 and the karat of the said Test Specimen 60 is read out. On removing the contact, the pressure on the Top Cap 22 is released and the Electrolyte 42 is reduxed into the Insertable Disposable Cartridge Assembly 40 conserving said Electrolyte 42 and flush cleaning the Electrolyte Feed Tube 32 and Porous Cap Assembly 50.

On exhaustion of the Electrolyte 42 from the used Insertable Disposable Cartridge Assembly 40, the Top Cap 22 of the Pencil Assembly 20 is snapped off and a fresh Insertable Disposable Cartridge Assembly 40 is inserted into the Cartridge Guide 30 which is rigidly held by the Retaining Ribs 28 at its top extremity and the Feed Tube 32, at its lower extremity.

FIG. 2A Porous Cap Assembly 50 and 2B the Slit Diaphragm 46

These FIGS. 2A and 2B are the major heart of the improvement design of the Gold Tester. The two components act symbiotically for a synergistic needed feature of the automatic self cleaning of the device as well as conservation of electrolyte and reproducible geometry of contacting surface. The use of a Porous Cap Assembly 50 instead of a permeable wick, such as a felt fiber, is an important innovation in this precious metal device technology. The long standing problems associated with (1) wetting the specimen sample with the electrolyte, (2) transporting fresh supplies of electrolyte to the galvanic cell and (3) defining the reproducible geometry of the wetted surface are herein alleviated by capturing the electrolyte onto the porous surface in this small galvanic cell of the Porous Cap Assembly 50. In addition, the Porous Cap Assembly 50 is easily cleaned of residual electrolyte by flushing or by customer purchased replacement parts.

This plan view of FIG. 2A POROUS CAP ASSEMBLY 50 also shows the circumferential placement of the Reference Electrode 52 and a pattern of orifices that assure a uniform and reproducible contact of electrolyte with a Test Specimen Electrode 60 assuring the calibration of the readout algorithm of the Electronics Program Box 10 is valid.

FIG. 2B THE SLIT DIAPHRAGM 46 shows a plan view of the Slit Diaphragm 46 which is a simple slit or cross slit that have pairs of lips. The Slit Diaphragm 46 is a redux device which causes an efflux of electrolyte on positive pressure and reflux on negative pressure. The Slit Lips 54 of said Slit Diaphragm 46 remain tightly shut when there is no net pressure assuring no leakage. Depressing the Top Cap 22 results in a delivery of electrolyte into the Porous Cap Assembly 50 and removal of pressure results in the redux of electrolyte and flush cleaning of all components distal to the to the Insertable Disposable Cartridge Assembly 40. Most input and output flow pumps require 2 valves, each permitting unidirectional flow. However, in this Gold Tester configuration, the simple Slit Diaphragm 46 suffices.

We claim:

1. A dynamic precious metal assay device for determining the karat of a precious metal test specimen where said device is combination of a sensor pencil assembly with an insertable disposable cartridge assembly containing electrolyte that may be ejected and on the distal lower end of said pencil assembly is a porous cap assembly holding a reference electrode wherein the said dynamic precious metal assay device comprises:

a flexing means on said an insertable disposable cartridge assembly which is capable of expelling said electrolyte by compressing flexing inward in response to an external pressure exercised by a user and self restoring back to its initial volume on relaxation of said pressure;

a slit diaphragm located between said insertable disposable cartridge assembly and said porous cap assembly which acts as a two way valve for the efflux of the said electrolyte to said porous cap assembly on compression of said insertable disposable cartridge assembly and reflux of unused electrolyte on removal of compression;

whereby the efflux is a precisely measured delivery of electrolyte to said porous cap assembly assuring a uniform wetting of said porous cap assembly so as to form an electrolytic cell with precision contact to said test specimen assuring accurate assay and on reflux of unused electrolyte through said slit diaphragm, a self cleaning of the dynamic precious metal assay device occurs.

2. The device of claim 1 wherein said slit diaphragm comprises a dual slit in the shape of a right angled equilateral cross.

3. The device of claim 1, wherein said flexing means on said insertable disposable cartridge assembly comprises an accordion fold.

\* \* \* \* \*